Nov. 30, 1926. Re. 16,489

A. L. HARRISON

THUMB SUCKING PREVENTER

Original Filed Feb. 25, 1924

INVENTOR.
ADRIA L. HARRISON

BY
Townsend, Loftus and Abbett
ATTORNEYS.

Reissued Nov. 30, 1926. Re. 16,489

UNITED STATES PATENT OFFICE.

ADRIA L. HARRISON, OF OAKLAND, CALIFORNIA.

THUMB-SUCKING PREVENTER.

Original No. 1,568,668, dated January 5, 1926, Serial No. 694,965, filed February 25, 1924. Application for reissue filed April 5, 1926. Serial No. 99,977.

My invention is an improved thumb sucking preventer particularly applicable to infants to prevent them from sucking the fingers.

The object of my invention is to provide a tube with suitable means to secure it to the side of the finger, and through which air is drawn as the child attempts to suck the finger, thus discouraging the child in its attempt, and breaking it of an injurious habit.

Obviously a multiplicity of ways may be employed to secure the tube to the finger, and in the drawing I have illustrated the preferred form, but in this application I desire to cover my invention in whatever form it may be embodied.

Figure 1:
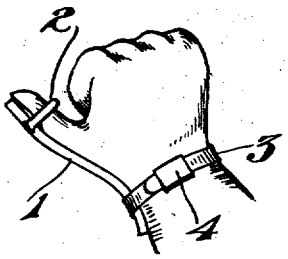
Figure 1 is a perspective view of my guard secured to the thumb of an infant.
Figure 2:
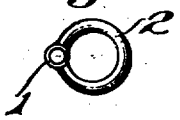
Figure 2 is a plan view of my guard.
Figure 3:
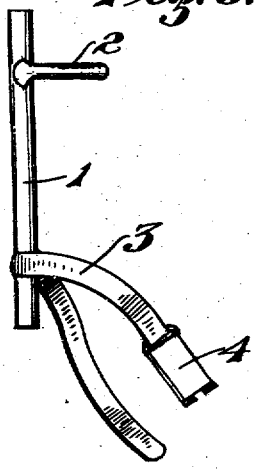
Figure 3 is a side view of the same.

Referring more particularly to the drawing, a flexible tube 1, which is preferably formed of rubber tubing, is secured to the thumb or finger of the infant. A ring 2 is secured to the tube 1 adjacent the upper end thereof, and the finger extends through said ring as shown.

This ring may be secured to the tube in any desired way, such as vulcanizing or molding the ring upon the tube. A strap 3 is secured to the tube 1 adjacent the lower end thereof, and a buckle 4 enables the strap to be secured about the arm of the infant. This strap may also be vulcanized or molded upon the tube, or otherwise suitably secured thereto.

Figure 4:
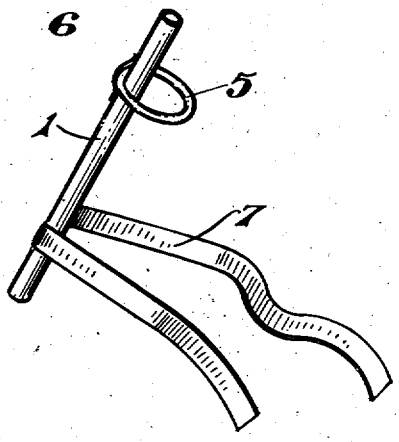
Figure 4 is a perspective view of a slightly modified form of my invention.

In the modified form shown in Figure 4 the ring 5 encircles the tube 1 and is secured thereto by vulcanizing a strip 6 over said ring and upon the tube. The strap 7 is secured to the lower part of the tube and is tied about the wrist of the wearer. The finger is slipped through the ring 2 or 5 and the strap 3 or 7 is secured to the arm. Thus the tube 1 is secured adjacent the finger of the infant.

When the infant attempts to suck the finger air is drawn through the tube, which discourages the habit.

The tube 1 being flexible gives absolute freedom to the hand and enables the child to play or move its fingers as desired.

Having described my invention, I claim:

1. A thumb sucking preventer comprising a tube and means to secure said tube to the side of the finger whereby air is drawn through the tube in the sucking of the finger.

2. A thumb sucking preventer comprising a flexible tube, and means to secure said tube to the side of the finger whereby air is drawn through the tube in the sucking of the finger.

3. A thumb sucking preventer comprising a tube adapted to fit alongside a finger, a ring secured to said tube and adapted to encircle the finger, and a strap secured to said tube and adapted to encircle the arm, said tube allowing air to be sucked therethrough.

4. A thumb sucking preventer comprising a tube adapted to fit alongside a finger, a ring secured to said tube and adapted to encircle the finger, and a strap secured to said tube, a buckle to which said strap is secured and whereby said strap is secured to the arm of the infant, said tube allowing air to be sucked therethrough.

5. A thumb sucking preventer comprising a tube having an air passageway formed longitudinally thereof, and means for securing said tube on the thumb of a person so that it will be inserted in the mouth of a person with the thumb so as to allow air to enter the mouth through said air passageway to prevent the formation of a partial vacuum in the mouth of said person.

ADRIA L. HARRISON.